United States Patent [19]
Kanner et al.

[11] Patent Number: 5,126,538
[45] Date of Patent: Jun. 30, 1992

[54] PLUG-IN TYPE CONTACT LENS DISINFECTOR

[75] Inventors: Rowland W. Kanner, Guntersville; Francis E. Ryder, Arab, both of Ala.

[73] Assignee: Ryder International Corporation, Arab, Ala.

[21] Appl. No.: 588,342

[22] Filed: Sep. 26, 1990

[51] Int. Cl.$^5$ .................. H05B 1/00; A61L 2/00
[52] U.S. Cl. ..................... 219/521; 219/386
[58] Field of Search ............ 219/385, 386, 521, 387, 219/438, 439

[56] References Cited

U.S. PATENT DOCUMENTS

| | | | |
|---|---|---|---|
| 2,513,919 | 7/1950 | Costello | 392/392 |
| 2,611,068 | 9/1952 | Wellens | 392/392 |
| 4,388,521 | 6/1983 | Thomas | 219/521 |
| 4,481,410 | 11/1984 | Bortnick | 219/521 |
| 4,529,868 | 7/1985 | Bowen | 219/521 |
| 4,659,911 | 4/1987 | Ryder et al. | 219/521 |
| 4,697,070 | 9/1987 | Kai | 219/521 |
| 4,743,738 | 5/1988 | Ryder et al. | 219/521 |
| 4,873,424 | 10/1989 | Ryder et al. | 219/521 |

*Primary Examiner*—Teresa J. Walberg
*Attorney, Agent, or Firm*—Trexler, Bushnell, Giangiorgi & Blackstone, Ltd.

[57] ABSTRACT

A plug-in type contact lens disinfecting apparatus includes a housing having formed therein a pair of receptacles, each having an open top portion for receiving a contact lens therewithin to be sterilized. A removable and releasable cap is provided for closing and sealing the open top portion of each of the receptacles and an electrically-energizable heater heats the receptacles to a preselected temperature for sterilizing contact lenses. An adaptor is provided for engagement with an electrical power source for delivering electrical power therefrom to the heater, and a cap guard is provided for operatively engaging the caps and the adaptor for preventing removal of the caps from the receptacles when the adaptor is engaged with said source of AC power. The apparatus may also include an arrangement for maintaining the contact lens receptacles in an upright position relative to the open tops thereof during engagement of the adaptor with an electrical power source which is oriented at either of two orientations substantially 90° apart.

25 Claims, 3 Drawing Sheets

PLUG-IN TYPE CONTACT LENS DISINFECTOR

BACKGROUND OF THE INVENTION

This application is directed generally to improvements in contact lens disinfecting apparatus and more particularly to a novel and improved plug-in type of contact lens disinfecting apparatus.

Soft and extended-wear types of contact lenses are widely used. These types of contact lenses are made from hydrophilic plastic porous material which can be formed to the desired lens curvature and thereafter will absorb water and become relatively soft and pliable. These types of lenses require frequent cleaning and disinfecting.

Several disinfecting methods have been developed and employed in conjunction with such soft and extended-wear contact lenses. The present invention pertains to a disinfecting unit or apparatus which utilizes a compact and easy to use plug-in type of unit. The unit comprises an electrical heating circuit, a heating element and receptacles for contact lenses. The invention may be utilized either with methods using a saline or other solution within the lens receptacle or methods in which the lenses are sterilized by a dry heat process.

One problem which has arisen with respect to some prior art disinfecting apparatus is that of preventing the user from removing the caps of the lens receiving receptacles while the unit is plugged into the wall socket. Such removal can cause the saline or other solution, in apparatus where said solution is utilized, to be disturbed and possibly contact and corrode other parts of the apparatus. In particular, some of the electrical parts of the unit which may be subject to damage and malfunction in the event of contact with or coating by various solutions.

Another problem is that of assuring the desired full cleaning time, with the contact lenses being retained within the heated receptacles for the proper amount of time necessary for proper cleaning and sterilization. Hence, it is desirable to prevent the user from removing the contact lenses from the apparatus when the unit is plugged in to perform the sterilizing process.

Spillage of cleaning solution may also occur in the event an attempt is made to add solution to the receptacles when the unit is plugged in. Moreover, it has been found that many users employ an extension cord, and will leave the unit plugged into the extension cord at all times. Hence, it is desirable to prevent access to the receptacles and maintain the lids in a closed position when the plug-in type unit is engaged either with a wall outlet or an extension cord, and to effectively require that the unit be removed from the wall outlet or extension cord in order to accomplish both placement and removal of both contact lenses and solution before and after the sterilizing process.

A related problem is that of maintaining the lens receptacles in an upright position during the sterilization process. In general, such plug-in type disinfector units are designed to plug into standard household AC wall outlets. Such outlets are commonly arranged in one of two orientations which are separated by substantially 90° of arc with respect to the required plug alignment for mating with the outlet. It is desirable, however, that the lens receptacles be kept in an upright position with the top openings and their covering caps oriented vertically upwardly, without regard for the relative orientation of the outlet into which the plug-in type disinfector is inserted.

OBJECTS AND SUMMARY OF THE INVENTION

It is a general object of this invention to provide a novel and improved plug-in type contact lens disinfecting apparatus which overcomes the above-noted problems of the prior art.

A related object is to provide a plug-in type contact lens disinfecting apparatus which requires removal of the apparatus from a source of AC power prior to removing cap portions thereof for the introduction and removal of contact lenses and/or sterilizing solution.

A further object is to provide a plug-in type contact lens disinfecting apparatus which is configured for holding the lens receptacles in a desired upright position without regard for the relative orientation of the wall outlet into which the unit is plugged during the disinfecting or sterilizing operation.

Briefly, and in accordance with the foregoing objects, the invention relates to an improvement in a plug-in type contact lens disinfecting apparatus of the type having a housing formed therein; a pair of receptacles each having an open top portion for receiving a contact lens therewithin to be sterilized; a removable and resealable cap for closing and sealing the open top portion of each of said receptacles, and electrically-energizable heating means for heating said receptacles to a preselected temperature for sterilizing contact lenses therewithin. The improvement comprises adaptor means for engagement with an electrical power source for delivering power therefrom to said heating means. Cap guard means may be provided for operatively engaging said caps and said adaptor means for preventing removal of said caps from said receptacles when said adaptor means is engaged with said electrical power source. The apparatus may include alignment means for maintaining said contact lens receptacles in an upright position relative to the open tops thereof during engagement of the adaptor with an electrical power source which is oriented at either of two orientations.

BRIEF DESCRIPTION OF THE DRAWINGS

The features of the present invention which are believed to be novel are set forth with particularity in the appended claims. The organization and manner of the operation of the invention, together with further objects and advantages thereof may best be understood by reference to the following description, taken in connection with the accompanying drawings in which like reference numerals identify like elements, and in which:

DETAILED DESCRIPTION OF THE ILLUSTRATED EMBODIMENT

Figure 1:
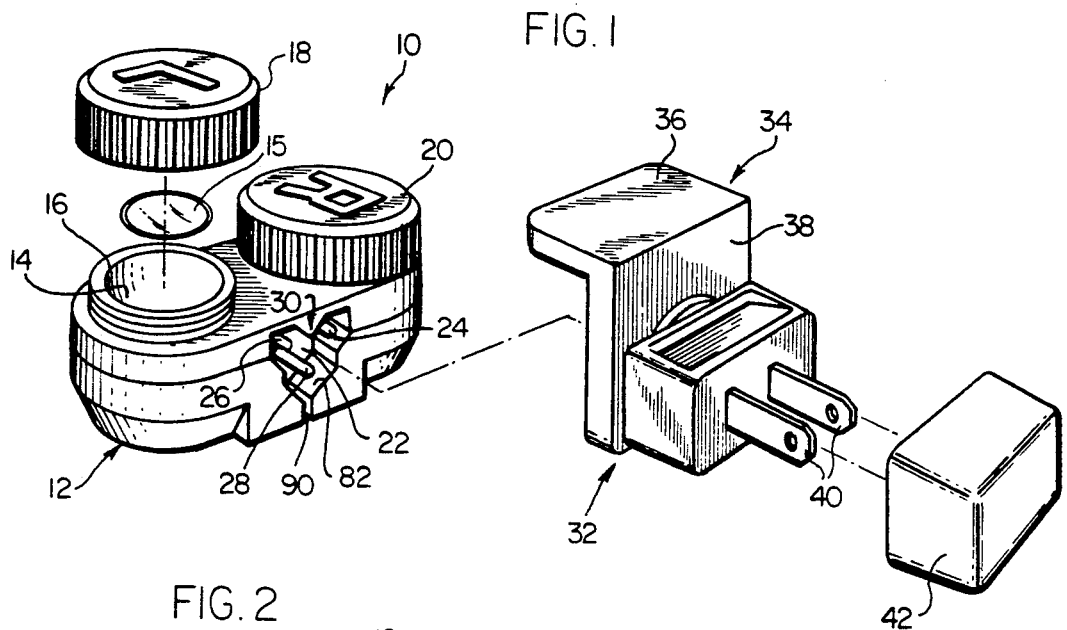
FIG. 1 is an exploded perspective view of a first embodiment of a pluq-in type contact lens disinfecting apparatus in accordance with the invention.
Figure 2:
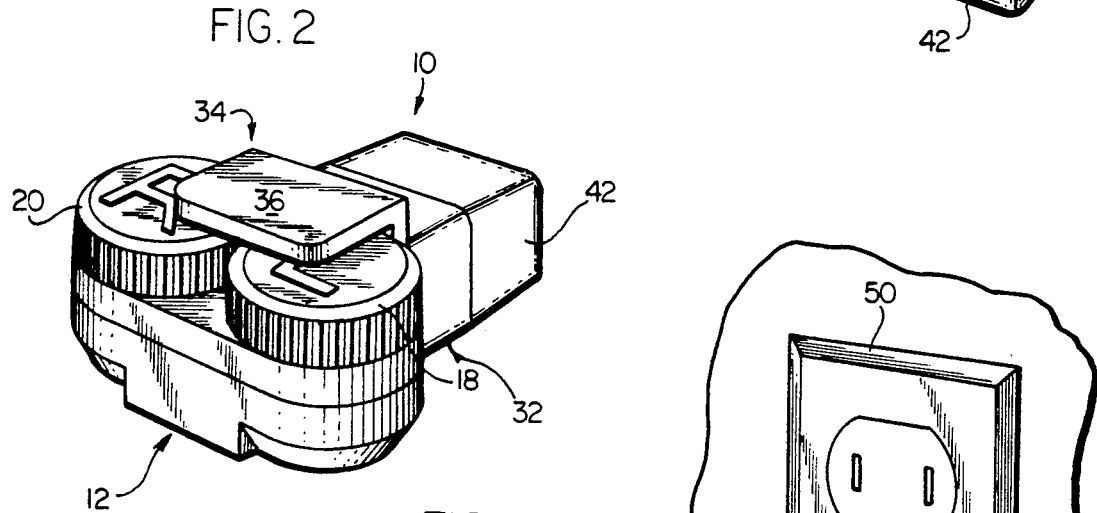
FIG. 2 is an assembled rear perspective view of the apparatus of FIG. 1.

Referring now to the drawings and initially to FIGS. 1 and 2, a plug-in type of contact lens disinfecting apparatus in accordance with one embodiment of the invention is indicated generally by the reference numeral 10. The apparatus 10 includes a housing 12 which has a pair of receptacles for receiving contact lenses 15 formed thereupon. Only one such receptacle 14 is shown, it being understood that a second, substantially identical receptacle is formed adjacent to the receptacle 14. These receptacles have open tops 16 and a removable and a resealable cap 18, 20 is provided for closing and sealing the open top of each of the receptacles.

Also contained within housing 12 is an electrically-energizable heating means 22 for heating the receptacles to a preselected temperature for sterilizing contact lenses therein. In the illustrated embodiment, only a portion of the heating means is shown, from which emanate one or more contacts 24, 26 and 28 of a power input receptacle 30 which are electrically connected with the heating means 22 for delivering suitable electrical power thereto.

The heating means may comprise a positive temperature coefficient (PTC) element, together with suitable energizing circuitry therefor. Such circuitry may also include suitable timer elements or other elements to control the duration of heating of the contact lens receptacles by the heating element. Exemplary forms of such positive temperature coefficient heating elements and suitable timer mechanisms or other control means and/or related circuits are shown for example in prior U.S. Pat. Nos. 4,659,911 and 4,743,738 which are commonly owned with this application.

Adaptor means which, in the embodiment illustrated in FIGS. 1 and 2, takes the form of a separate adaptor assembly 32, is provided for engagement with a source of electrical power, and preferably household AC power, for delivering the power therefrom to the heating means 22 by way of the power input receptacle 30. In the illustrated embodiment, the adaptor 32 includes a cap guard portion or cap guard means 34 for operatively engaging the caps 18 and 20 and the adaptor means 32 in such a manner as to prevent removal of the caps 18 and 20 from their associated receptacles when the adaptor 32 is engaged with a source of power, and while the housing 12 is engaged with the adaptor 32.

In the illustrated embodiment this cap guard means or member 34 comprises a generally L-shaped projecting member. Member 34 has a first surface or abutment portion 36 configured for overlying and engaging at least a portion of each of the caps 18 and 20, and a second substantially planar surface or portion 38 from which projects power source engagement means or a power input portion. In the illustrated embodiment, this power input portion comprises a pair of parallel projecting AC prongs 40 of suitable configuration for engagement with a standard household AC outlet, or extension cord or the like. An additional protective cover or cap member 42 is also provided for engaging and protecting the AC prongs 40 when the apparatus 10 is not in use; for example, during transport or storage thereof.

Figure 5:
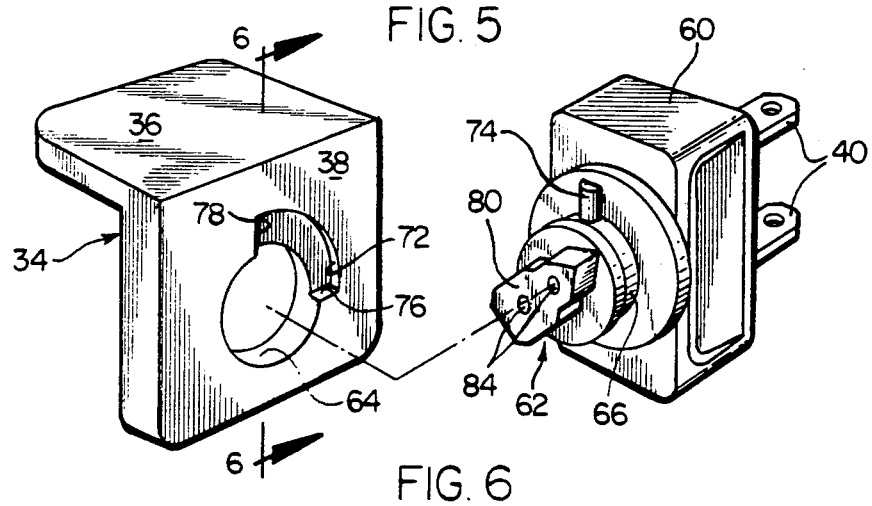
FIG. 5 is an exploded perspective view of an adaptor portion or assembly of the apparatus shown in FIGS. 1–4.
Figure 6:
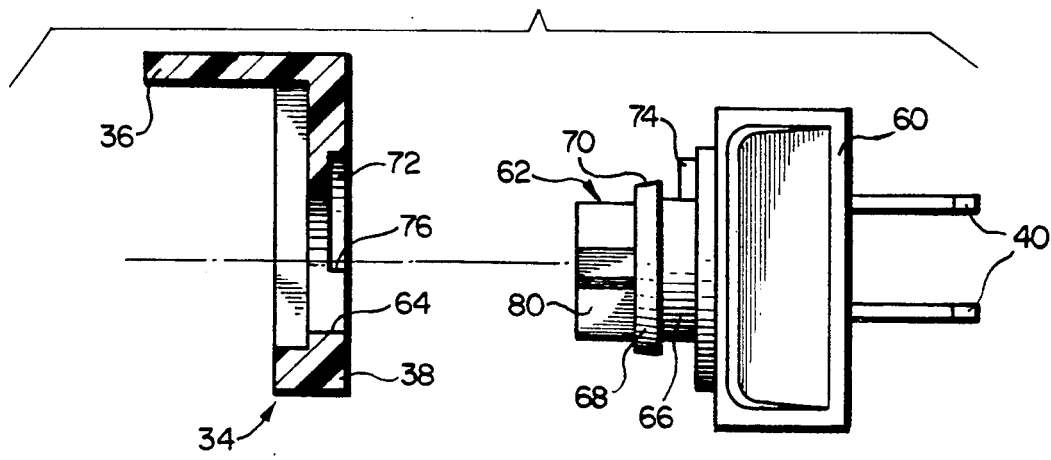
FIG. 6 is an exploded side elevation, partially in section, of the adaptor portion of FIG. 5.

In the illustrated embodiment, the respective surfaces 36 and 38 are operatively engaged by virtue of being integrally formed as a single piece, as is best shown in FIG. 5.

In the embodiment illustrated in FIGS. 1-6, the adaptor means 32 also includes alignment means for maintaining the contact lens receptacles in an upright position relative to their open tops during engagement of the adaptor 32 with a source of AC power, which is oriented at either of two orientations substantially 90° apart, This operation is further illustrated in FIGS. 3-6, to which reference is now invited.

Figure 3:
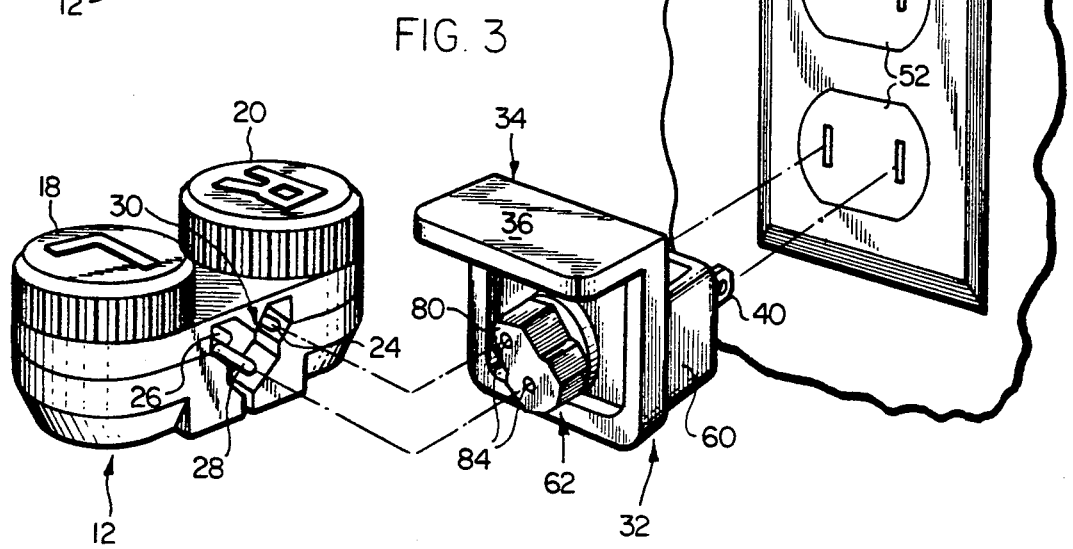
FIG. 3 is an exploded view of the apparatus of FIGS. 1 and 2 in cooperation with an AC wall outlet or receptacle having a first orientation.
Figure 4:
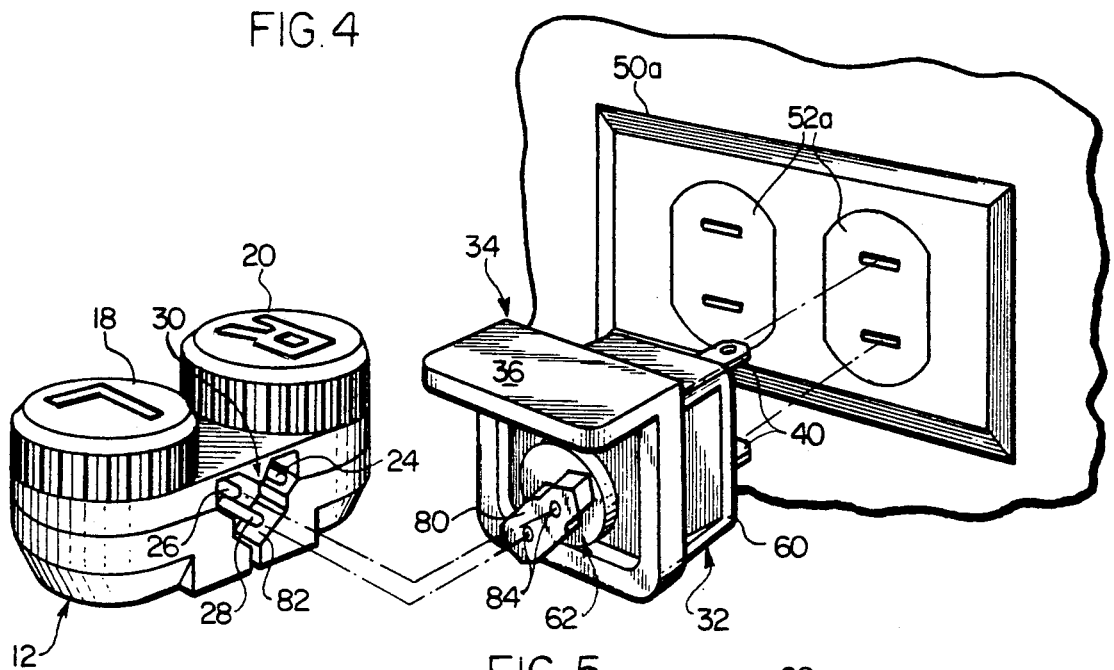
FIG. 4 is a view similar to FIG. 3 showing the apparatus of FIGS. 1 and 2 in use with a household wall outlet or receptacle having a second orientation.

Referring initially to FIGS. 3 and 4, two typical orientations of typical AC power outlets 50 and 50a are illustrated. It will be seen that the receptacles 52 and 52a of these respective outlets are oriented in positions or orientations which are substantially 90° apart. That is, the orientation of outlets 52a of FIG. 4 is rotated substantially 90° from that of the outlets 52 of FIG. 3.

The alignment means or arrangement includes a first or adaptor alignment portion formed on the adaptor means or assembly 32. This alignment portion comprises an AC line member or portion 60 which mounts the previously mentioned AC male plug member or prongs 40, and a power input jack member or portion 62 which is electrically coupled to the AC line member 60 and is also mechanically engaged for movement in unison therewith. Cooperatively, a mounting member which comprises the previously described member 34, further mounts the AC line portion 60 and power input jack 62 for rotation about substantially a 90° arc.

In the illustrated embodiment this rotation is accomplished by means of a through opening 64 in the mounting member 34 which snappingly or otherwise rotatably receives a complementary surface portion 66 formed intermediate the AC line member 60 and input jack 62. The complementary portion 66 may further be provided at its leading edge a radially enlarged portion 68 which is further provided with a beveled peripheral surface 70 to encourage snapping engagement and retention of the portion 66 with through opening 64, in the manner of a lead-in portion. However, other arrangements may be employed for rotatably coupling the members 60 and 62 with the mounting member 64 without departing from the invention.

A 90° arc of movement between the mounting member 64 and the members 60, 62 is defined by an arcuate groove or cut-out portion 72 formed in a surface of the mounting member 34 which groove extends over a substantially 90. arc adjacent the through opening 64. A complementary abutment or stop surface is formed adjacent the surface 66 in the form of a raised rib 74 which is positioned for riding within the groove 72. The raised rib 74 thus defines opposite limits of rotational movement of the members 60 and 62 relative to the mounting member 64 as it engages opposite terminal end portions or surfaces 6, 78 of the recessed groove or cut-out portion 72. Other arrangements for defining such a 90° arc of rotation of members 60, 62 relative to member 64 may be employed without departing from the invention. The alignment means or arrangement further includes the power input jack or portion 62 previously described which is formed in the housing 12. This power input jack 30 is of complementary form for receiving a mating end portion 80 of the power input jack 62. It will be noted that the external shape or configuration of this portion 80 is complementary with an internal surface portion 82 of the receptacle 30 formed in housing 12. The mating end portion 80 of power input jack 62 includes a pair of recessed or female-type electrical contacts 84 which are of complementary form and spacing for engagement with two of the three electrical contacts 24, 26 and 28 of the receptacle 30.

In this regard, contacts 84 may mate either with contacts 24 and 28 or with contacts 26 and 28 depending upon the orientation in which the member 80 is turned relative to the mounting member 34 and the housing 12. It will be seen that in FIG. 3 one such orientation is indicated, wherein the receptacles 84 receive contacts 24 and 28, whereas in FIG. 4, a second orientation, substantially 90° of arc away from that shown in FIG. 3 is illustrated wherein the receptacles 84 receive contacts 26 and 28. It will be further noted that the external configuration of the mating portion 80 will matingly engage with the internal surface 84 of receptacle 30 in either of the two positions indicated at FIGS. 3 and 4, respectively.

In this regard, the power input receptacle 30 has its electrical contacts 24, 26 and 28 in two orientations which are angularly spaced by a 90° arc, and which thereby generally define or are arranged adjacent apices of a right triangle, which right triangle is generally inverted relative to the upright position of the case 12 and its receptacle 14 and caps 18, 20 as described hereinabove. Hence the contacts 84 of the power input jack 62 are arranged for mating engagement with the power input receptacle contact 28 which is adjacent the right angle apex of the triangle defined by the contacts 24, 26 and 28 and with another of these contacts adjacent one of the other apices of the triangle defined thereby. Which of contacts 24 and 26 is used depend upon the orientation of the adaptor assembly or means 32 relative to the electrical power source, such as wall outlet 50, when the housing 12 is held in its upright position.

In the embodiment illustrated in FIGS. 1-6, the housing 12 further includes a small drain slot or opening 90 at a bottom portion of the power input receptacle 30. That is, slot 90 extends downwardly from the right angle apex of the triangle defined thereby, to permit ready drainage of any liquid which may inadvertently enter receptacle 30 during use and handling of the disinfecting apparatus, when the housing is in the upright position, as assured by the above-described arrangement, in use.

Figure 7:
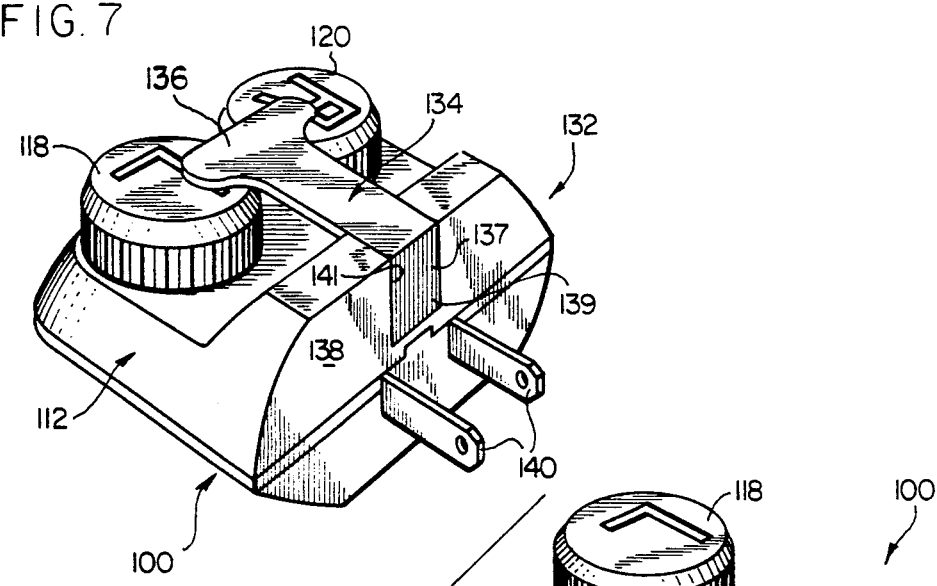
FIG. 7 is a front perspective view of a plug-in type contact lens disinfecting apparatus in accordance with a second embodiment of the invention.
Figure 8:
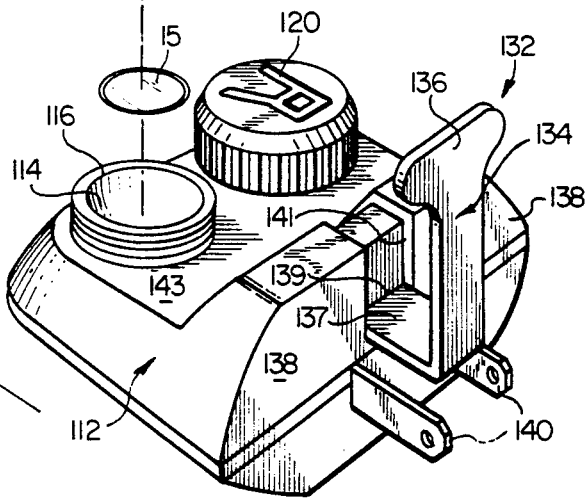
FIG. 8 is a front perspective view similar to FIG. 7 showing a changed position of portions of the apparatus of FIG. 7.
Figure 9:
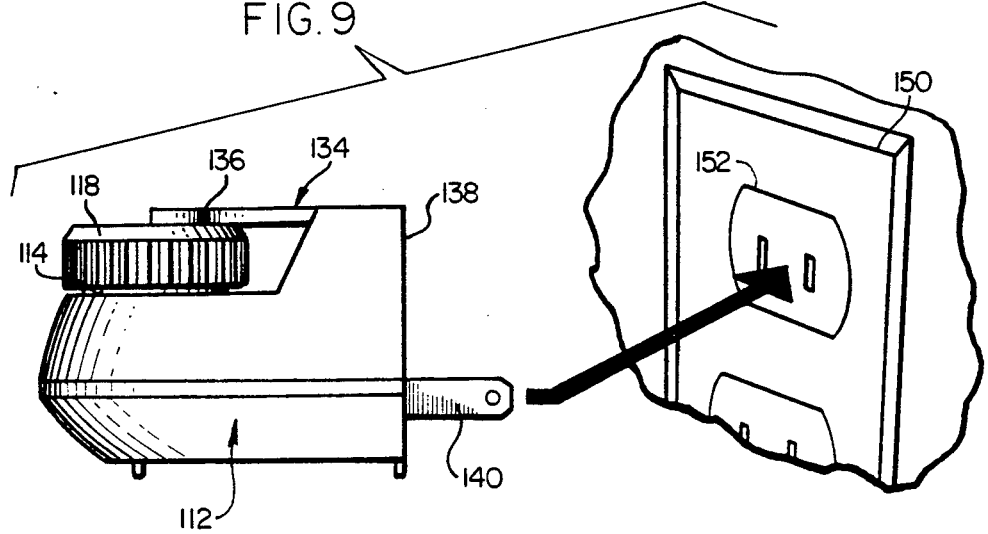
FIG. 9 is a side elevational view of the apparatus of FIGS. 7 and 8 indicating use of the same with a source of AC power such as a household wall outlet.

Referring now to FIGS. 7-9, a second embodiment of a plug-in type of contact lens disinfecting apparatus in accordance with the invention is illustrated. This second embodiment or apparatus is designated generally by the reference numeral 100. In similar fashion to the embodiment described hereinabove, the apparatus 100 includes a housing 112 which has formed therein a pair of contact lens receptacles, only one such receptacle 114 having an open top 116, being visible in FIG. 8. The receptacles are provided with similar caps 118, 120 for sealingly releasably engaging the same to hold a contact lens and a quantity of suitable fluid or solution therewithin.

In the embodiment of FIGS. 7-9, the adaptor means or portion 132 is integrally formed with the housing 112. This adaptor portion includes a planar surface 138 from which project power source engagement means in the form of a pair of spaced prongs or contacts 140 of the form for engaging an ordinary household AC outlet, or extension cord or the like. A typical AC wall outlet 140 having a socket 152 is shown in FIG. 9. A cap guard means or member 134 is engaged with the adaptor means or portion 132 and also with the housing 112 and takes the form of a generally L-shaped member which is coupled for hinged movement relative to the surface 138. The projecting member or guard 134 includes an abutment portion 136 for overlying and engaging at least a portion of each of the caps 118 and 120, and a locking portion 137 which extends from the abutment portion 136 into alignment with planar surface 138, for engagement between the surface 138 and electrical power source, such as AC wall receptacle 150, when the adaptor portion is engaged therewith.

A hinge arrangement or hinge means 139 is defined between a terminal end portion of the locking portion 137 and a like inner or terminal end portion of a groove or recess 141, which is formed in the surface 138 for receiving portion 137 in flush coplanar engagement therewith when in the first or locked position indicated in FIGS. 7 and 9. In this regard, this hinged mounting thereby defines two operative positions of the cap guard means 132, including a first or blocking position as illustrated in FIGS. 7 and 9, wherein the locking portion 137 is in coplanar alignment with the surface 138 and the abutment portion 136 engages and overlies a portion of each of the caps. In a second operative position indicated in FIG. 8, the member 134 is hinged through substantially 90° of movement. A lesser arc of hinged movement may be employed without departing from the invention so long as the movement is sufficient to release the engagement of locking portion 136 with caps 118 and 120 to a sufficient degree which will permit removal and/or replacement of the caps relative to the housing 112. Such a condition is indicated generally in FIG. 8.

Accordingly, in the illustrated embodiment, the housing includes a second surface 143 which is oriented at substantially right angles to the planar surface 138, below which the receptacles are formed and from which the caps 118, 120 project when engaged. Cooperatively, the guard means or member 134 is substantially L-shaped and the abutment portion 137 is thereby oriented or formed at substantially at right angles to the locking portion 136.

While particular embodiments of the invention have been shown and described in detail, it will be obvious to those skilled in the art that changes and modifications of the present invention, in its various aspects, may be made without departing from the invention in its broader aspects, some of which changes and modifications being matters of routine engineering or design, and others being apparent only after study. As such, the scope of the invention should not be limited by the particular embodiment and specific construction described herein but should be defined by the appended claims and equivalents thereof. Accordingly, the aim in the appended claims is to cover all such changes and modifications as fall within the true spirit and scope of the invention.

The invention is claimed as follows:

1. An improved plug-in type contact lens disinfecting apparatus of the type having electrically energizable heating means for sterilizing contact lenses therewithin, said improved apparatus comprising: a housing having formed therein a pair of receptacles, each having an open top portion for receiving a contact lens therewithin to be sterilized; a removable and resealable cap which closes and seals the open top portion of each of said receptacles, adaptor means which engages with an electrical power source deliver power therefrom to said heating means, and cap guard means operatively coupled with said adaptor means, said cap guard means being configured and located to engage and prevent removal of said caps from said receptacles when said adaptor means is engaged with said housing and which permits removal of said caps from said receptacles only when said adaptor means is disengaged from said housing.

2. An apparatus according to claim 1, and further including alignment means for maintaining said contact lens receptacles in an upright position relative to the open tops thereof during engagement of the adaptor means with an electrical power source which is oriented at either of two orientations.

3. Apparatus according to claim 2 wherein said alignment means comprises an adaptor alignment portion formed on said adaptor means and including an AC line portion having a household AC male plug member formed thereon, a power input jack electrically coupled and mechanically engaged for movement in unison with said AC line portion and a mounting member for mounting said AC line portion and said power input jack for rotation about substantially a 90° arc.

4. Apparatus according to claim 3 wherein said cap guard means comprises a projecting guard portion formed on said mounting member for overlying and engaging at least a portion of each of said caps when said housing is engaged with said adaptor means.

5. Apparatus according to claim 3 wherein said alignment means further comprises a housing alignment portion formed on said housing and including a power input receptacle of complementary form for engagement with said power input jack for delivering AC power to said heating means.

6. Apparatus according to claim 5 wherein said housing defines a drain opening communicating with said power input jack.

7. Apparatus according to claim 5 wherein said power input receptacle includes a plurality of electrical contacts arranged in two orientations angularly spaced by a 90° arc so as to receive said power input jack in each of two corresponding orientations separated by substantially 90° of arc.

8. Apparatus according to claim 7 wherein said plurality of contacts comprise three electrical contacts arranged adjacent apices of a right triangle.

9. Apparatus according to claim 8 wherein the right angle apex of said right triangle is inverted relative to the upright position of said contact lens receptacles.

10. Apparatus according to claim 8 wherein said power input jack comprises a pair of spaced apart contacts configured for mating engagement with the one of the power input receptacle contacts adjacent the right angle apex of said triangle defined thereby and with one of the power input receptacle contacts adjacent one of the other apices of said triangle, depending upon the orientation of said adaptor means relative to said electrical power source when said housing is in the upright position relative to said contact lens receptacles.

11. An improvement in a plug-in type contact lens disinfecting apparatus of the type including a housing having formed therein a pair of receptacles, each having an open top portion for receiving a contact lens therewithin to be sterilized; a removable and resealable cap for closing and sealing the open top portion of each of said receptacles; and electrically-energizable heating means for heating said receptacles to a preselected temperature for sterilizing contact lenses therewithin; said improvement comprising: adaptor means separate from said housing which engages with an electrical power source and selectively engageable with said housing to deliver electrical power to said heating means and alignment means which maintains said contact lens receptacles in an upright position relative to the open tops thereof during engagement of the adaptor means with the housing and with an electrical power source which is oriented at either of two orientations.

12. Apparatus according to claim 12 wherein said alignment means comprises an adaptor alignment portion formed on said adaptor means and including an AC line portion having a household AC male plug member formed thereon, a power input jack electrically coupled and mechanically engaged for movement in unison with said AC line portion and a mounting member for mounting said AC line portion and said power input jack for rotation about substantially a 90° arc.

13. Apparatus according to claim 12 wherein said cap guard means comprises a projecting guard portion formed on said mounting member for overlying and engaging at least a portion of each of said caps when said housing is engaged with said adaptor means.

14. Apparatus according to claim 13 wherein said alignment means further comprises a housing alignment portion formed on said housing and including a power input receptacle of complementary form for engagement with said power input jack for delivering AC power to said heating means.

15. Apparatus according to claim 14 wherein said housing defines a drain opening communicating with said power input jack.

16. Apparatus according to claim 14 wherein said power input receptacle includes a plurality of electrical contacts arranged in two orientations angularly spaced by a 90° arc so as to receive said power input jack in each of two corresponding orientations separated by substantially 90° of arc.

17. Apparatus according to claim 16 wherein said plurality of contacts comprise three electrical contacts arranged adjacent apices of a right triangle.

18. Apparatus according to claim 17 wherein the right angle apex of said right triangle is inverted relative to the upright position of said contact lens receptacles.

19. Apparatus according to claim 17 wherein said power input jack comprises a pair of spaced apart contacts configured for mating engagement with the one of the power input receptacle contacts adjacent the right angle apex of said triangle defined thereby and with one of the power input receptacle contacts adjacent one of the other apices of said triangle, depending upon the orientation of said adaptor means relative to said electrical power source when said housing is in the upright position relative to said contact lens receptacles.

20. An improvement in a plug-in type contact lens disinfecting apparatus of the type including a housing having formed therein a pair of receptacles, each having an open top portion for receiving a contact lens therewithin to be sterilized; a removable and resealable cap for closing and sealing the open top portions of said receptacles; and electrically-energizable heating means for heating said receptacles to a preselected temperature for sterilizing contact lenses therewithin; said improvement comprising: power input means which engages with an electrical power source deliver power therefrom to said heating means, and cap guard means operatively coupled with said power input means, said cap guard means being configured and located to engage and prevent removal of said caps from said receptacles when said power input means is engaged with an electrical power source and which permits removal of said caps from said receptacles only when said power input means is disengaged from an electrical power source.

21. Apparatus according to claim 20, wherein said power input means includes a planar surface having a power input portion formed thereon and wherein said cap guard means comprises a projecting member having an abutment portion configured for overlying and engaging at least a portion of each of said caps and operatively engaged with said planar surface for preventing movement thereof away from engagement with said electrical power source.

22. Apparatus according to claim 21, wherein said power input means is formed integrally with said housing and wherein said projecting member further includes a locking portion which extends from said abutment portion into alignment with said planar surface for engagement between said planar surface and said electrical power source, and further including hinge means for hingedly coupling said projecting member relative to said planar surface for movement between a first position wherein said locking portion is substantially coplanar with said planar surface and said abutment portion engages and overlies at least a portion of each said cap and a second position wherein said locking portion extends away from said planar surface and said abutment portion is out of engagement with said caps.

23. Apparatus according to claim 22 wherein said planar surface is defined upon said housing and wherein said housing includes a second surface oriented at substantially right angles to said planar surface and in which said open tops of said receptacles are formed, and wherein said guard means is a substantially L-shaped member having said abutment portion thereof and said locking portion thereof formed substantially at right angles to each other.

24. Apparatus according to claim 22 wherein said planar surface further includes a recess for receiving said locking portion of said guard means therewithin when the same is in the said first position.

25. Apparatus according to claim 24 wherein said locking portion has a terminal end part and wherein said hinge means is formed between said terminal end part of said locking portion and a corresponding terminal end portion of said recess.

* * * * *

UNITED STATES PATENT AND TRADEMARK OFFICE
CERTIFICATE OF CORRECTION

PATENT NO. : 5,126,538
DATED : June 30, 1992
INVENTOR(S) : Rowland W. Kanner and Francis E. Ryder It is certified that error appears in the above-identified patent and that said Letters Patent is hereby corrected as shown below:

Column 4, Line 54 "substantially 90. arc adjacent the through opening 64." should be -- substantially 90° arc adjacent the through opening 64.--

Column 4, Line 61 "end portions or surfaces 6, 78 of the recessed groove or " should be -- end portions or surfaces 76, 78 of the recessed groove or --

Column 8, Line 14 "Apparatus according to claim 12 wherein said " should be -- Apparatus according to claim 11 wherein said --

Signed and Sealed this

Seventh Day of September, 1993

*Attest:*

BRUCE LEHMAN

*Attesting Officer*     *Commissioner of Patents and Trademarks*